(12) United States Patent
Stensrud

(10) Patent No.: US 9,802,950 B2
(45) Date of Patent: Oct. 31, 2017

(54) MONO-ETHERS OF ISOHEXIDES AND PROCESS FOR MAKING THE SAME

(71) Applicant: ARCHER DANIELS MIDLAND COMPANY, Decatur, IL (US)

(72) Inventor: Kenneth Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/777,680

(22) PCT Filed: Mar. 5, 2014

(86) PCT No.: PCT/US2014/020579
§ 371 (c)(1),
(2) Date: Sep. 16, 2015

(87) PCT Pub. No.: WO2014/168698
PCT Pub. Date: Oct. 16, 2014

(65) Prior Publication Data
US 2016/0289241 A1    Oct. 6, 2016

Related U.S. Application Data

(60) Provisional application No. 61/809,949, filed on Apr. 9, 2013.

(51) Int. Cl.
*C07D 493/04*    (2006.01)
(52) U.S. Cl.
CPC ................ *C07D 493/04* (2013.01)

(58) Field of Classification Search
CPC .................................................. C07D 493/04
See application file for complete search history.

(56) References Cited

PUBLICATIONS

Zhu, Y., et al. "Isosorbide as a novel polar head derived from renewable resources. Application to the design of short-chain amphiphiles with hydrotropic properties." Green Chemistry. (2008), vol. 10, pp. 532-540.*
Lavergne, et al. "Synthesis and foaming properties of new anionic surfactants based on a renewable building block: Sodium dodecyl isosorbide sulfates." J. of Colloid and Interface Science. (2011), vol. 360, pp. 645-653.*
Zhu, Y., et al. "Isosorbide as a novel polar head derived from renewable resources. Application to the design of short-chain amphiphiles with hydrotropic properties." J. Royal Society of Chemistry, Green Chemistry. (2008), vol. 10, pp. 532-540.*
Lavergne, A., et al. "Synthesis and foaming properties of new anionic surfactants based on a renewable building block: Sodium dodecyl isosorbide sulfates." J. Colloid and Interface Science 360. (2011), pp. 645-653.*

* cited by examiner

*Primary Examiner* — Noble Jarrell
*Assistant Examiner* — John S Kenyon
(74) *Attorney, Agent, or Firm* — William B. Miller

(57) ABSTRACT

A method of making a mono-ether of an isohexide and art assemblage of novel. Song-chain isohexide mono-ethers are described. In particular, the method involves reacting an isohexide stereoisomer with a Bronsted base and an alkyl species. The resultant mono-ethers can serve as attractive antecedents or chemical scaffolds for making a derivative compound, such as various amphiphiles with potential uses as surfactants, dispersants, and lubricants, among others.

2 Claims, No Drawings

MONO-ETHERS OF ISOHEXIDES AND PROCESS FOR MAKING THE SAME

PRIORITY CLAIM

The present application is a national stage entry of International Application No. PCT/US2014/20579, filed 5 Mar. 2014, which claims benefit of U.S. Provisional Patent Application No. 61/809,949, filed on Apr. 9, 2013, the contents of which each are herein incorporated by this reference.

FIELD OF INVENTION

The present application relates to cyclic bifunctional ethers of isohexides that are useful as amphiphilic compounds and intermediates generally, and to particular methods by which such compounds are made.

BACKGROUND

Traditionally, polymers and commodity chemicals have been prepared from petroleum-derived feedstock. As petroleum supplies have become increasingly costly and difficult to access, interest and research has increased to develop renewable or "green" alternative materials from biologically-derived sources for chemicals that will serve as commercially acceptable alternatives to conventional, petroleum-based or -derived counterparts, or for producing the same materials as produced from fossil, non-renewable sources.

One of the most abundant kinds of biologically-derived or renewable alternative feedstock for such materials is carbohydrates. Carbohydrates, however, are generally unsuited to current high temperature industrial processes. As compared to petroleum-based, hydrophobic, aliphatic, or aromatic feedstocks having as low degree of functionalization, carbohydrates such as polysaccharides are complex, over-functionalized hydrophilic materials. As a consequence, researchers have sought to produce biologically-based chemicals that can be derived from carbohydrates, but which are less highly functionalized, including more stable bi-functional compounds, such as 2,5-furandicarboxylic acid (FDCA), levulinic acid, and 1,4:3,6-dianhydrohexitols.

1,4:3,6-Dianhydrohexitols (also referred to herein as isohexides) are derived from renewable resources from cereal-based polysaccharides. Isohexides embody a class of bicyclic furanodiols that derive from the corresponding reduced sugar alcohols (D-sorbitol, D-mannitol, and D-iditol respectively). Depending on the chirality, three isomers of the isohexides exist, namely: A) isosorbide, B) isomannide, and C) isoidide, respectively the structures of which are illustrated in Scheme 1.

Scheme 1:

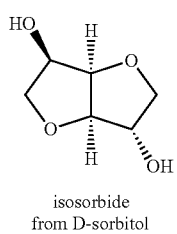

isosorbide
from D-sorbitol

A

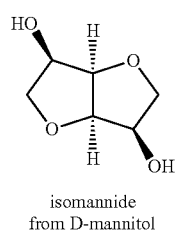

isomannide
from D-mannitol

B

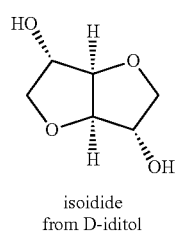

isoidide
from D-iditol

C

These molecular entities have received considerable interest and are recognized as valuable, organic chemical scaffolds for a variety of reasons. Some beneficial attributes include relative facility of their preparation and purification, the inherent economy of the parent feedstocks used in their preparation, owing not only to their renewable biomass origins, which affords great potential as surrogates for non-renewable petrochemicals, but perhaps most significantly the intrinsic chiral bi-functionalities that permit a virtually limitless expansion of derivatives to be designed and synthesized.

The isohexides are composed of two cis-fused tetrahydrofuran rings, nearly planar and V-shaped with a 120° angle between rings. The hydroxyl groups are situated at carbons 2 and 5 and positioned on either inside or outside the V-shaped molecule. They are designated, respectively, as endo or exo. Isoidide has two exo hydroxyl groups while hydroxyl groups are both endo in isomannide, and one exo and one endo hydroxyl group in isosorbide. The presence of the exo substituents increases the stability of the cycle to which it is attached. Also exo and endo groups exhibit different reactivities since they are more or less accessible depending on the steric requirements of the derivatizing reaction.

As interest in chemicals derived from natural resources is increases, potential industrial applications have generated interest in the production and use of isohexides. For instance, in the field of polymeric materials, the industrial applications have included use of these diols to synthesize or modify polycondensates. Their attractive features as monomers are linked to their rigidity, chirality, non-toxicity, and the fact that they are not derived from petroleum. For these reasons, the synthesis of high glass transition temperature polymers with good thermo-mechanical resistance and/or with special optical properties is possible. Also the innocuous character of the molecules opens the possibility of applications in packaging or medical devices. For instance, production of isosorbide at the industrial scale with a purity satisfying the requirements for polymer synthesis suggests that isosorbide can soon emerge in industrial polymer applications. (See e.g., F. Fenouillot et al., "Polymers From Renewable 1,4:3,6-Dianhydrohexitols (Isosorbide, Isomanide and Isoidide): A Review," PROGRESS IN POLYMER SCIENCE, vol. 35, pp 578-622 (2010), or X. Feng et al., "Sugar-based Chemicals for Environmentally sustainable Applications," CONTEMPORARY SCIENCE OF POLYMERIC MATERIALS, Am. Chem. Society, December 2010, contents of which are incorporated herein by reference.)

Another application that has received limited interest involves isohexide-derived amphiphiles, compounds that manifest discrete hydrophilic and hydrophobic zones that afford unique inter and intramolecular self-assemblies in response to environmental stimuli. Conventionally, isohexide-based amphiphilic esters are predisposed to hydrolyze, particularly in commonly employed, non-neutral aqueous matrices. An alternative domain can offer a much greater robustness to hydrolytic conditions include alkyl ethers.

To better utilize isohexides as a green feedstock, a clean and simple method of preparing the isohexides as a mono-ether that can be subsequently modified to synthesize other compounds would be welcome by those in the green or renewable chemicals industry.

SUMMARY OF THE INVENTION

The present invention, in part, provides a method for preparing a mono-ether of an isohexide. The method involves reacting an isohexide with a Brønsted base and an alkyl-X species, according to the following equation:

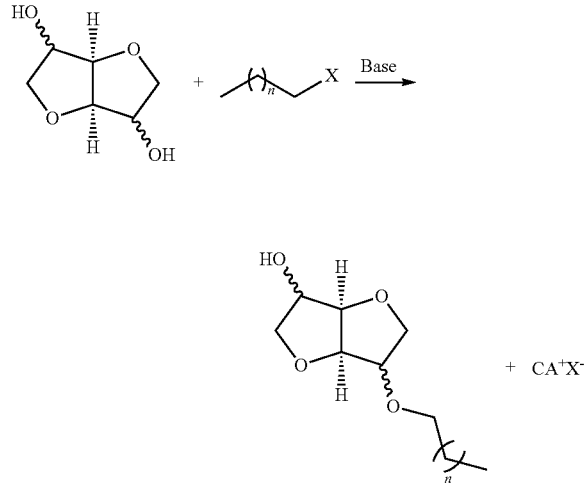

wherein: "X" is a leaving group; "n" is an integer from 0 to 23, and "CA" is a conjugate acid of the Brønsted base. The leaving group "X" is at least one of the following: a halide, mesylate (OMs), tosylate (OTs), and trifluoromethanesulfonate, also known by the name triflate (OTf). The isohexide stereoisomer and a conjugate acid of the Brønsted base each have an acid disassociation constant pKa, and the absolute value of the difference ($\Delta$ pKa=pKa Brønsted base–pKa isohexide —OH) between the pKa of the isohexide stereoisomer and the conjugate acid of the Brønsted base is at least 0. The synthesis reaction can produce a variety of mono-alkyl ethers in a controlled manner which maximizes the yield of mono-ether product.

In another aspect, the invention pertains to compounds that can be derivatized from the isohexide mono-ethers. These compounds have a general formula as follows:

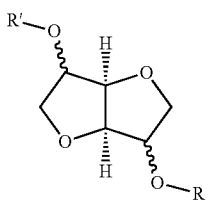

wherein R is H, or $C_3$-$C_{22}$; and R' is $SO_3H$ and corresponding anion, $PO_3H_2$ and corresponding anion(s), and an alkyl, alkyl-ether or alkyl-polyether with a chain of $C_4$-$C_{25}$.

DETAILED DESCRIPTION OF THE INVENTION

Section I.—Description

As biomass derived compounds that afford great potential as surrogates for non-renewable petrochemicals, 1,4:3,6-dianhydrohexitols are a class of bicyclic furanodiols that are valued as renewable molecular entities. (For sake of convenience, 1,4:3,6-dianhydrohexitols will be referred to as "isohexides" or "isohexide stereoisomer" in the Description hereinafter.) As referred to above, the isohexides are good chemical platforms that have recently received interest because of their intrinsic chiral bi-functionalities, which can permit a significant expansion of both existing and new derivative compounds that can be synthesized.

Isohexide starting materials can be obtained by known methods of making respectively isosorbide, isomannide, or isoidide. Isosorbide and isomannide can be derived from the dehydration of the corresponding sugar alcohols, D-sorbitol and D mannitol. As a commercial product, isosorbide is also available easily from a manufacturer. The third isomer, isoidide, can be produced from L-idose, which rarely exists in nature and cannot be extracted from vegetal biomass. For this reason, researchers have been actively exploring different synthesis methodologies for isoidide. For example, the isoidide starting material can be prepared by epimerization from isosorbide. In L. W. Wright, J. D. Brandner, *J. Org. Chem.*, 1964, 29 (10), pp. 2979-2982, epimerization is induced by means of Ni catalysis, using nickel supported on diatomaceous earth. The reaction is conducted under relatively severe conditions, such as a temperature of 220° C. to 240° C. at a pressure of 150 atmospheres. The reaction reaches a steady state after about two hours, with an equilibrium mixture containing isoidide (57-60%), isosorbide (30-36%) and isomannide (5-7-8%). Comparable results were obtained when starting from isoidide or isomannide. Increasing the pH to 10-11 was found to have an accelerating effect, as well as increasing the temperature and nickel catalyst concentration. A similar disclosure can be found in U.S. Pat. No. 3,023,223, which proposes to isomerize isosorbide or isomannide. More recently, P. Fuertes proposed a method for obtaining L-iditol (precursor for isoidide), by chromatographic fractionation of mixtures of L-iditol and L-sorbose (U.S. Patent Publication No. 2006/0096588; U.S. Pat. No. 7,674,381 B2). L-iditol is prepared starting from sorbitol. In a first step sorbitol is converted by fermentation into L-sorbose which is subsequently hydrogenated into a mixture D-sorbitol and L-iditol. This mixture is then converted into a mixture of L-iditol and L-sorbose. After separation from the L-sorbose, the L-iditol can be converted into isoidide. Thus, sorbitol is converted into isoidide in a four-step reaction, in a yield of about 50%. (The contents of the cited references are incorporated herein by reference).

A. Mono-Ether Synthesis Reaction

The present invention provides, in part, an efficient and facile process for making mono-ethers of isohexides. The process involves the reaction of an isohexide stereoisomer with a Brønsted base and an alkyl or aliphatic species. The isohexide stereoisomer is at least one of the following: isosorbide, isomannide, and isoidide or a mixture of two or all three of these. The respective isohexide compounds can be obtained either commercially or synthesized from relatively inexpensive, widely-available biologically-derived feedstocks. The general reaction is presented in Scheme 1.

Scheme 1: General Synthesis Reaction

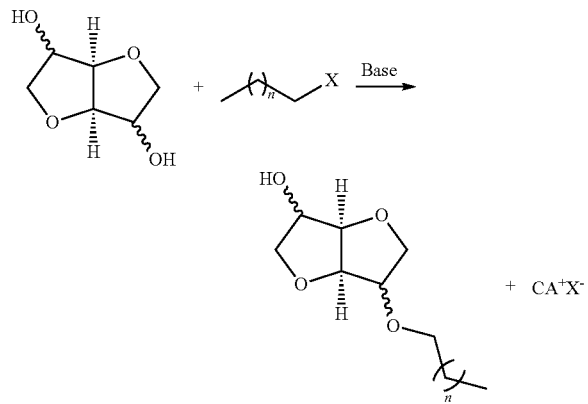

wherein: "X" is a leaving group, "n" is an integer from 0 to 23, and "CA" is a conjugate acid of the Brønsted base. Typically, "n" is an integer from 2, 3 or 4 through 18, 19, or 20, inclusive of any value in between. The total length of the aliphatic portion of the alkyl-X species can range from about $C_2$ or $C_3$ up to about $C_{22}$ or $C_{25}$. Typically, the carbon chain is between about $C_2$, $C_4$ or $C_6$ to about $C_{16}$, $C_{17}$ or $C_{18}$, or a combination of different ranges therein. In the synthesis, the isohexide stereoisomer and alkyl species are reacted generally in 1:1 molar equivalents.

In the alkyl-X species, "X" serves as a leaving group or nucleofuge. In certain embodiments, "X" is an alkyl halide, such as a chloride, bromide or iodide. As one of the more economical and commercial sources of aliphatic halides, bromides are more favored. Aliphatic iodides and chlorides can be used also, but are not as favored commercially. In other embodiments, one can employ other nucleofuges, such as mesylates

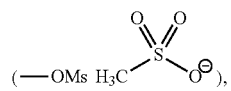

tosylates

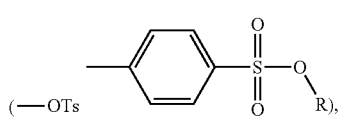

or trifluoromethanesulfonates, also known by the name triflates

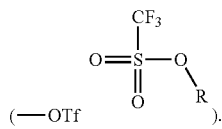

These species, however, are not as readily available commercially as the alkyl-halides and may need to be synthesized.

The isohexide stereoisomer and a conjugate acid of the Brønsted base each have an acid dissociation constant pKa, wherein an absolute value of the difference ($\Delta pKa = pKa$ Brønsted base–pKa isohexide —OH) between the pKa values of the isohexide stereoisomer and the conjugate acid of said Brønsted base is at least 0. As used herein, the absolute value (or modulus) |x| of a real number x refers to the non-negative value of x without regard to its sign. Namely, |x|=x for a positive x, |x|=−x for a negative x, and |0|=0. For example, the absolute value of 3 is 3, and the absolute value of −3 is also 3. Hence, the absolute value of a number may be thought of as its distance from zero. The absolute value of x is always either positive or zero, but never negative. Each hydroxyl moiety of isohexide has an individual pKa, and the average pKa of isohexide is about 16. Generally, the conjugate acids of suitable Brønsted bases can have a pKa from a minimum of about 4 or 5 to a maximum of about 30 or 32. Typically, the pKa of the conjugate acid of the Brønsted base is about 9, 10 or 12 up to about 20-28. In certain preferred embodiments, the pKa of the conjugate acid of the Brønsted base is greater than 16 (e.g., about 17 or 18 to about 20 or 25). In certain embodiments, suitable Brønsted bases may include, for example: t-butoxides (pKa=17), hindered or tertiary amines (e.g., tri-ethylamine, di-isopropyl-ethylamine, or tri-propylamine), hydroxides, or carbonates.

Although various Brønsted bases are suitable and can perform well in the present reaction, not all kinds of species should be used. One of the issues facing the synthesis of mono-ethers from isohexide stereoisomers has been to avoid uncontrolled or rapid depotonation of both hydroxyl moieties of the isohexide molecule, since both hydroxyl moieties have equal reactivity, and the reaction is entirely collision based. The present synthesis process attempts to minimize the generation of di-ether side products. As the positive difference between the pKa of the alcohol moieties of the isohexide stereoisomer and mild Brønsted base increases, deprotonation is favored and the reaction kinetics is driven to the right to produce the mono-ether. However, Brønsted bases that exhibit positive ΔpKa values that are too great relative to that of the isohexide stereoisomer are not desirable for a controlled synthesis and tend to work less effectively at generating good yields of target isohexide mono-ethers. When positive ΔpKa is too great, double deportonation of isohexide —OH moieties (dianion) tends to occur, which gives rise to reaction conditions that generates the predominantly di-ethers, such as illustrated in Comparative Example 1.

In Comparative Example 1, below, a di-ether is the primary product when an alkyl hydride is used as the Brønsted base, even when stringently controlling reaction conditions. This result, it is believed, stems from a heightened reactivity due to a sizable ΔpKa between the hydride and isohexide. As it is known, hydrides are more basic than alcohols (by ≥18-20 orders of magnitude); consequently, hydrides will deprotonate almost immediately each of the alcohol moieties of the isohexide without stereo-specificity, irrespective of the solution temperature, thus producing a reaction setting that favors di-ethers. Hence, in general, Brønsted bases with higher pKa values such as alkyl hydrides (pKa=42), alkyl lithiums (pKa≥53), alkyl magnesiums (pKa=51), alkyl cuprates, or metal amides should be avoided.

Thus, the conjugate acid of Brønsted bases should have a pKa that is not more than about 15 or 16 orders of magnitude greater than the pKa of the alcohol (hydroxyl) moieties of an isohexide which is about 16-17. According to certain iterations, the absolute value of the difference in pKa. (ΔpKa) is in a range from about 1 or 2 to about 8 or 10 (e.g., desirably about 1-9, 1-7, 1-3, 2-4, 2-5, or 2-6), so as to better control the deprotonation of the isohexide molecule in favor of a single over a double deprotonation.

In embodiments that use conjugate acids of Brønsted bases having a pKa greater (i.e., about 17 or greater) than that of the alcohol moieties of the isohexide, the reactions are highly exothermic, necessitating control of the initial temperature conditions. The reagents are added initially at low temperatures of about 1° C. or less. Then, the reaction temperature is allowed gradually to rise to ambient room temperature (e.g., ~20° C.-25° C.). In certain embodiments, the initial temperature is typically in a range between about 0° C. or about –5° C. and about –65° C. or –78° C. In some embodiments, the initial temperature can range between about –2° C. or –3° C. and about –60° C. or –70° C. (e.g., –10° C., –15° C., –25° C., or –55° C.). Particular temperatures can be from about –7° C. or –8° C. to about –40° C. or –50° C. (e.g., –12° C., –20° C., –28° C. or –36° C.). In other words, the cool to cold initial temperature helps lower the initial energy of the system, which increases control of the kinetics of the reaction, so that one can produce selectively more of the mono-ether species than of the di-ether species. In an embodiment, for example, the Brønsted base is potassium t-butoxide; t-butanol, the conjugate acid of i-butoxide, has a $pK_a$ of about 18 or 19, as illustrated in Scheme 2, below.

Scheme 2:

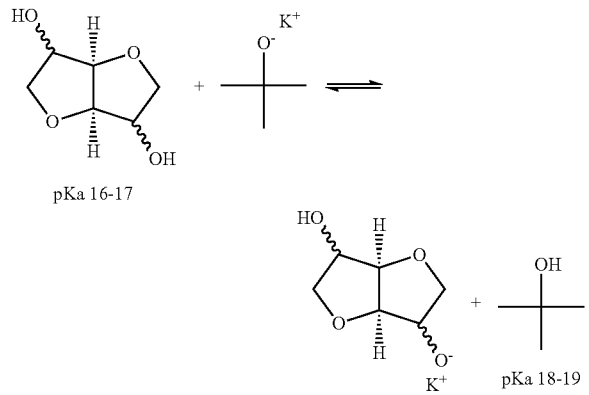

pKa 16-17 pKa 18-19

The embodiments of this kind, in which the value of the ΔpKa of the alcohol moieties of the isohexide and the Brønsted bases is positive and will self-propel the reaction to the ether product, are preferred.

One can make use of a relatively slow induction period (i.e., between about 20 or 30 minutes up to about 40 or 45 minutes), which permits the base to dissolve in the polar aprotic solvent and the acid-base equilibration to occur. Slow or gradual addition of reagents at lower temperatures will minimize unwanted side products that arise from elimination. During the induction period the desired mono-ether product is formed in large excess without need for additional energy input. As another benefit, a relatively low reaction temperature reduces the propensity for base-induced eliminations, which can form alkenes from alkyl-halides.

In other embodiments, when conjugate acids of non-nucleophilic bases that have a pKa of either the same or lower value an the pKa of the alcohol moieties of the isohexide, external energy input is required to drive the reaction forward, ameliorating the competitiveness of isohexide alkylation with isohexide reprotonation. As the pKa differences between isohexide —OH and Brønsted bases will not react readily to generate significant amounts of oxide, the inherently slower kinetics can be helpful in controlling mono-ether synthesis. Hence, in reactions using a) a species with a pKa of about 4-9 will require heating the reaction to at least about 50° C. or 60° C. to about 70° C. 80° C., more; b) a species with a pKa of about 10-16 will require some heating to about ambient room temperature or up to about 50° C. With proper modulation of the higher reaction temperatures, one can tailor the reaction to generate less undesired side products.

An excess amount of Brønsted base can be employed with some species such as hindered amines or carbonates. Any acid that may be formed in the reaction (e.g., protonated form of isosorbide) immediately will be deprotonated, hence the pH will be alkaline (i.e., greater than 7).

An organic solvent is used to facilitate the reaction. In some embodiments, the organic solvent is a non-nucleophilic species with a dielectric constant (∈, permittivity) of at least 20. Typically the permittivity of a suitable solvent is within a range from about 20 to about 50, with solvent having a higher permittivity being more preferred. Some suitable polar, aprotic organic solvents include for example, in the order of utility in terms of decreasing dielectric constants: dimethyl sulfoxide (DMSO) (∈=46.7), nitromethane ($CH_3NO_2$) (∈=39.4), N,N-dimethylacetamide (∈=37.8), acetonitrile ($CH_3CN$) (∈=37.5), N,N-di methyl-formamide (DMF) (∈=36.7) hexamethylphosphoramide (HMPA) (∈=31.3), or acetone (∈=20.7). Hence, for example, DMSO is preferred over nithromethane, over DMF, etc. In an example, reactions conducted in dimethylformamide, DMF, furnished the highest yield of isohexide mono-ethers, although several solvents were evaluated, including acetone, tetrahydrofuran, acetonitrile, methanol and ethanol.

As an exception to these general parameters, tetrahydrofuran (THF) (∈=7.58) or 1,4 dioxane (∈=2.25) also may be used as a solvent, even though they possess a relatively low dielectric constant, because of the very polarized C—O bonds which will induce significant negative charge on the oxygen atoms, enabling the solvent to complex with cations, thus freeing the anionic base to better deprotonate the hydroxyl moieties of the isohexides.

Neither alcohol-based nor aqueous solvents are suitable for the present reactions. Although alcohols are organic, nonetheless, they will react with the alkyl species which is undesired. Water is not a compatible solvent because it is nucleophilic and can react with the alkyl halides or sulfonates to form alcohols. Also, alkyl halides or sulfonates tend to be insoluble in water. In certain embodiments, water can solvate the Brønsted base, for instance, a t-butoxide and deter its basicity.

In addition to being a clean and simple synthesis process, the present method of synthesis possesses several other advantages. For instance, in certain preferred embodiments, the bulkiness of a t-butoxide limits its inherent nucleophilicity, which decreases the likelihood of forming t-butyl-ethers with alkyl halides or other species. A gradual addition of alkyl-halides (e.g., drop-wise or in portions), for instance, can prevent saturation and permit the desired nucleophilic substitutions to occur at least as readily as other random, collision-induced (elimination) processes.

Depending on the particular alkyl species, one may run the present synthesis reaction for a time period that generates the most mono-ether. The reaction time can be, for instance, between about 30 minutes up to about 48 hours or more. The type of alkyl species used in the synthesis is the time-sensitive or yield-limiting reagent for making the mono-ether. For example, certain alkyl reagents having shorter (e.g., $\leq C_{10}$ or $C_{11}$) aliphatic carbon chains can react for shorter durations, as they tend to react more quickly than longer (e.g, $>C_{12}$ or $C_{14}$) aliphatic species. This phenomenon may be due in part to steric effects, but is not necessarily direct a linear relationship.

The present synthesis process can result in satisfactory yields of corresponding mono-ethers, as demonstrated in the accompanying examples. The process is able to produce primarily isohexide mono-alkyl ethers in reasonably high molar yields, depending on the kind of alkyl species, from about 10% or 12% to about 50% or 60% from the starting materials, typically about 15% or 17% to about 43% or 47%. With proper control of the reaction conditions and time, one can achieve yields up to about 70%-75% of the mono-ether species. Di-ethers will be the predominant side products (e.g., ~25-30%), and the quantity of di-ether will be typically the same as unreacted isohexides.

B. Mono-Ethers of Isohexide Stereoisomers

In another aspect, the present invention pertains to the isohexide mono-ethers prepared from the reaction of an isohexide stereoisomer with a Brønsted base and an alkyl species. As the process for preparing these molecular entities is new, the various isohexide mono-ethers prepared according to the present invention are novel compositions of matter. The isohexide mono-ether has a general formula:

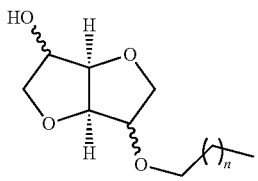

wherein "n" is an integer from 0 to 23. One can employ these mono-ethers as a chemical scaffold or platform from which various kinds of derivative compounds can be prepared. Illustrative examples of some mono-ethers are presented in the Section II.—Examples below.

C. Derivative Compounds from Isohexide Mono-Ethers

In another aspect, the present invention provides derivative compounds that can be synthesized from the mono-ethers of isohexides. The derivative of the mono-ether has a general formula as follows:

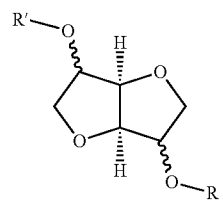

wherein R is H, or $C_3$-$C_{22}$; and R' is $SO_3H$ and corresponding anion, $PO_3H_2$ and corresponding anion(s), and an alkyl, alkyl-ether or alkyl-polyether with a chain of $C_4$-$C_{25}$. Particular examples of R' as an alkyl-polyether can include $CH_2CH_2OCH_2CH_2OH$ and $CH_2CH_2OCH_2CH_2OCH_2CH_2OH$.

The derivative of mono-ethers that can be made according to the present invention may include various organic moieties, for example, one or more of the following R-groups: alkyl, allyl, aryl, or benzyl groups. Of particular interest, however, are mono-alkyl ethers. Mono-alkyl ethers of isohexides are desirable as precursors for amphiphiles (i.e., a molecule having a water-soluble or hydrophilic polar moiety and a hydrophobic organic moiety) or other derivative chemical compounds, such as surfactants or dispersants.

Although isohexide stereoisomers (i.e., isosorbide, isomannide, and isoidide) bear a signature fused antiparallel furofuran core, the three dimensional arrangement of hydroxyl moieties in each are different. The difference in geometric orientation between the functional groups imparts unique amphiphilic properties to the mono ethers of the isohexides. Hence, an aspect of the present invention relates to the synthesis of a variety of either short ($\leq C_6$) medium ($C_7$-$C_{12}$) or long ($\geq C_{13}$) carbon chain isosorbide, isomannide and isoidide monoalkyl ethers. These scaffolds present attractive antecedents to different amphiphiles with potential uses, for instance, as surfactants, hydrophiles (e.g., carbon chain $C_4$-$C_8$), organogels, theology adjustors, dispersants, emulsifiers, lubricants, plasticizers, chiral auxiliary compound with specific stereochemistry, among others. The derivatives may be produced efficiently up to quantitative yields from the mono-alkyl ether of isosorbide, isomannide, isoidide or a mixture of two or all three of these.

Section II.—Examples

The present invention is further illustrated with reference to the following examples. The examples herein were prepared according to the following general reaction:

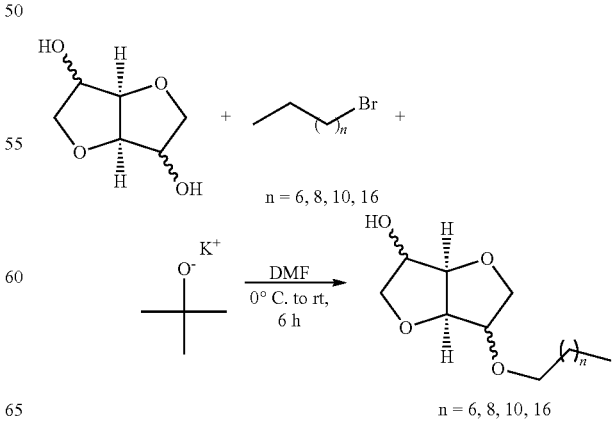

A. Isomannide

Example 1: Synthesis of (3R,3aR,6R,6aR)-6-(octyloxy)hexahydrofuro[3,2]furan-3-ol

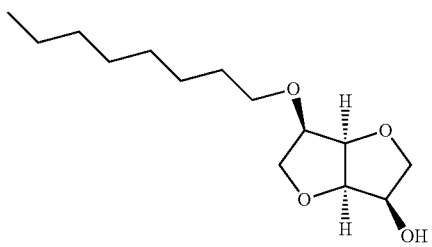 [SMILES: CCCCCCCCO[C@@H]1CO[C@H]2[C@@H]1OC[C@H]2O]

Experimental: A 20 cc scintillation vial equipped with a ½" egg-shaped PTFE coated magnetic stir bar was charged with 108 mg of isomannide (0.96 mmol), 104 mg of potassium t-butoxide (0.96 mmol) 5 of dry DMF and stirred for 30 minutes. A rubber septum was then fitted to the vial mouth, the vial immersed in an ice/brine bath for 5 minutes, and 220 µL of octylbromide (1.25 mmol) added dropwise, followed by warming to room temperature and vigorous stirring for 6 hours. At this time, an aliquot was removed, decocted, and quantitatively analyzed by GC/MS. The resulting spectrum evinced a signal for the title compound at 16.2 min that corresponded to 29% mass yield. Residual isomannide, octylbromide, and some elimination product, oct-1-ene was also observed. Approximately ~12% composition consisted of the octyl-diether of isomannide near 23 min. Thin-layer Chromatography (1:1 hexanes/ethyl acetate) employing a cerium molybdate stain manifested four salient spots, one near the solvent front that was consistent with octylbromide (and oct-1-ene) one with an rf=0.71 relating the octyl-diether variant, one with rf=0.29, consistent with the title compound, and one near the baseline, denoting unreacted isomannide.

Example 2: Synthesis of (3R,3aR,6R,6aR)-6-(decyloxy)hexahydrofuro[3,2-b]furan-3-ol

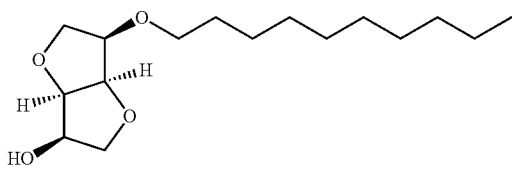 [SMILES: CCCCCCCCCCO[C@@H]1CO[C@H]2[C@@H]1OC[C@H]2O]

Experimental: An oven dried, 50 cc boiling flask equipped with a ⅞" octagonal. PTFE coated magnetic stir bar was charged with 1.00 g of isomannide (6.8 mmol), 921 mg of potassium t-butoxide (8.2 mmol) and 25 of dry DMF, then capped with a rubber septum. After the mixture had been stirred for 30 minutes, the flask was immersed in a ice/brine bath for 5 min, and 1.57 mL of decylbromide (7.5 mmol) added dropwise via syringe through the septum. The mixture was stirred vigorously for a period of 6 h, after which an aliquot was removed, decocted, and quantitatively analyzed by GC/MS. The resulting spectrum evinced a signal for the title compound at 19.2 min that corresponded to ~31% mass yield. Residual isomannide, decylbromide, and some elimination product, dec-1-ene was also observed in the chromatogram. An exiguous amount of decyl diether of isomannide, at ~25 min, was espied. Thin-layer chromatography (1:1 hexanes/ethyl acetate) employing cerium molybdate stain manifested three prominent spots, one near the solvent front consistent with decylbromide (and dec-1-ene) one with an rf=0.38 consistent with the title compound and one near the baseline, representing unreacted isomannide.

Example 3: Synthesis of (3R,3aR,6R,6aR)-6-(dodecyloxy)hexahydrofuro[3,2-b]furan-3-ol

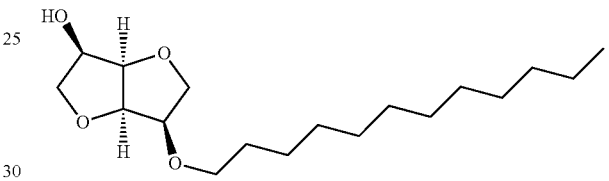

Experimental: A 20 cc scintillation vial equipped with as egg-shaped PTFE coated magnetic stir bar was charged with 121 mg of isomannide (0.83 mmol), 121 mg of potassium t-butoxide (1.08 mmol), 5 mL of dry DMF and stirred for 30 minutes. A rubber septum was then fitted to the vial mouth, the vial immersed in an ice/brine bath for 5 minutes, and 260 µL of dodecyl bromide (1.08 mmol) added dropwise, followed by warming to room temperature and vigorous stirring for 6 hours. At this time, an aliquot was removed, decocted, and quantitatively analyzed by GC/MS. The resulting spectrum evinced a signal for the title compound at 20.6 min that corresponded to ~27% mass yield. Residual isomannide, dodecyl bromide and some elimination product, dodec-1-ene was also observed. Thin-layer chromatography (1:1 hexanes/ethyl acetate) employing cerium molybdate stain manifested three salient spots, one near the solvent front consistent with dodecylbromide (and dodec-1-ene), one with rf=0.39 consistent with the title compound and one near the baseline, signifying unreacted isomannide.

Example 4: Synthesis of (3R,3aR,6R,6aR)-6-(octadecyloxyl)hexahydrofuro[3,2-b]furan-3-ol

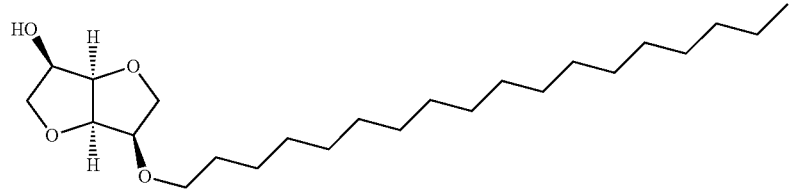 [SMILES: CCCCCCCCCCCCCCCCCCO[C@@H]1CO[C@H]2[C@@H]1OC[C@H]2O]

Experimental: A 20 cc scintillation vial equipped with a ½" egg-shaped PTFE coated magnetic stir bar was charged with 110 mg of isomannide (0.75 mmol), 110 mg of potassium t-butoxide (0.98 mmol), 5 mL of dry DMF and stirred for 30 minutes. The vial was capped and immersed in an ice/brine bath for 5 minutes, and 326 mg of octadecyl bromide (0.98 mmol) added in portions followed by warming to room temperature and vigorous stirring for 6 hours. At this time, an aliquot was removed, decocted, and quantitatively analyzed by GC/MS. The resulting spectrum evinced a signal for the title compound at 24.9 min that corresponded to ~22% mass yield. Residual isomannide, octdecyl bromide and some elimination product, octadec-1-ene was also observed. Thin-layer chromatography (1:1 hexanes/ethyl acetate) employing cerium molybdate stain manifested three salient spots, one near the solvent front consistent with octadecylbromide (and octadec-1-ene), one with rf=0.46 consistent with the title compound and one near the baseline, specifying remnant isomannide.

B. Isoiodide

Example 5: Synthesis of (3S,3aR,6S,6aR)-6-(octyloxy)hexahydrofuro[3,2-b]furan-3-ol

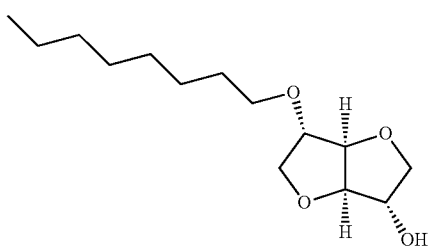 [SMILES: CCCCCCCCO[C@H]1CO[C@H]2[C@@H]1OC[C@@H]2O]

Experimental: A 20 cc scintillation vial equipped with a ½" egg-shaped PTFE coated magnetic stir bar was charged with 141 mg of isoidide (0.96 mmol) 140 mg of potassium t-butoxide (1.25 mmol), 5 mL of dry DMF and stirred for 30 minutes. A rubber septum was then fitted to the vial mouth, the vial immersed in an ice/brine bath for 5 minutes, and 220 µL of octylbromide (1.25 mmol) added dropwise, followed by warming to room temperature and vigorous stirring for 6 hours. At this time, an aliquot was removed, decocted, and quantitatively analyzed by GC/MS. The resulting spectrum evinced a signal for the title compound at 17.8 mM that corresponded to ~36% mass yield. Residual isoidide, octylbromide and some elimination product, oct-1-ene was also observed. Approximately ~10% composition consisted of the octyl diether variant of isoisoidide near 22 min. Thin-layer chromatography (1:1 hexanes/ethyl acetate) employing cerium molybdate stain manifested four salient spots, one near the solvent front consistent with octylbromide (and oct-1-ene), one with an rf=0.75 relating the octyl-diether analog, one with rf=0.32 consistent with the title compound and one near the baseline, indicating remnant isoidide.

Example 6: Synthesis of (3S,3aR,6S,6aR)-6-(decyloxy)hexahydrofuro[3,2-b]furan-3-ol

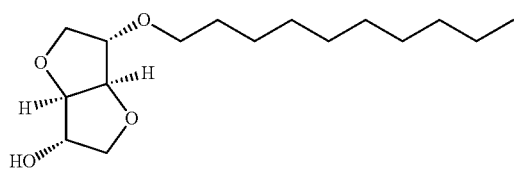

Experimental: A 20 cc scintillation vial equipped with a ¼" egg-shaped PTFE coated magnetic stir bar was charged with 134 mg of isoidide (0.92 mmol), 123 mg of potassium t-butoxide (1.10 mmol), 5 mL of dry IMF and stirred for 30 minutes. A rubber septum was then fitted to the vial mouth, the vial immersed in an ice/brine bath for 5 minutes, and 210 µL of decylbromide (1.01 mmol) added dropwise, followed by warming to room temperature and vigorous stirring for 6 hours. At this time, an aliquot was removed, decocted, and quantitatively analyzed by GC/MS. The resulting spectrum evinced a signal for the title compound at 19.3 min that corresponded to ~32% mass yield. Residual isoidide, decylbromide, and some elimination product, dec-1-ene also evinced signals in the chromatogram. A small amount of decyl diether of isoidide, at ~24.8 min, was descried. Thin-layer chromatography (1:1 hexanes/ethyl acetate) employing cerium molybdate stain manifested four salient spots, one near the solvent front consistent with decylbromide (and dec-1-ene), one with an rf=0.80 representing the decyl-diether variant, one with an rf=0.34 consistent with the title compound and one near the baseline demonstrating residual isoidide.

Example 7: Synthesis of (3S,3aR,6S,6aR)-6-(dodecyloxy)hexahydrofuro[3,2-b]furan-3-ol

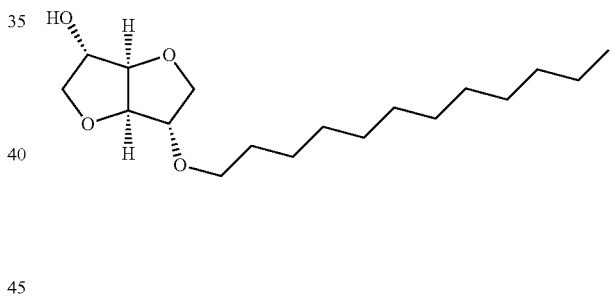

Experimental: A 20 cc scintillation vial equipped with a ½" egg-shaped PTFE coated magnetic stir bar was charged with 270 mg of isoidide (1.85 mmol), 271 mg of potassium t-butoxide (2.41 mmol), 5 of dry DMF and stirred for 30 minutes. A rubber septum was then fitted to the vial mouth, the vial immersed in an ice/brine: bath for 5 minutes, and 583 µL of dodecyl bromide (2.41 mmol) added dropwise, followed by warming to room temperature and vigorous stirring for 6 hours. At this time, an aliquot was removed, decocted, and quantitatively analyzed by GC/MS. The resulting spectrum evinced a signal for the title compound at 20.7 min that corresponded to ~34% mass yield. Residual isoidide, dodecyl bromide and some elimination product, dodec-1-ene was also observed. Thin-layer chromatography (1:1 hexanes/ethyl acetate) employing cerium molybdate stain manifested three salient spots, one near the solvent front consistent with dodecylbromide (and dodec-1-ene), one with rf=0.42 consistent with the title compound and one near the baseline, representing residual isoidide.

Example 8: Synthesis of (3S,3aR,6S,6aR)-6-(octadecyloxy)hexahydrofuro[3,2-b]furan-3-ol

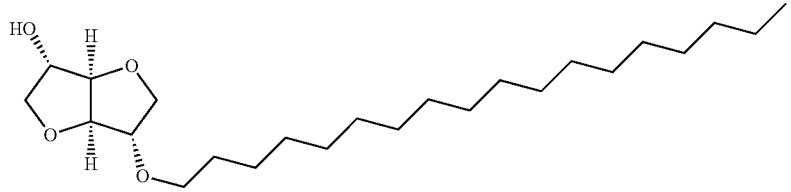 [SMILES: CCCCCCCCCCCCCCCCCCO[C@H]1CO[C@H]2[C@@H]1OC[C@@H]2O]

Experimental: A 20 cc scintillation vial equipped with a ½" egg-shaped PTFE coated magnetic stir bar was charged with 111 mg of isoidide (0.76 mmol), 110 mg of potassium t-butoxide (0.98 mmol), 5 mL of dry DMF and stirred for 30 minutes. The vial was capped and immersed in an ice/brine bath for 5 minutes, and 326 mg of octadecyl bromide (0.98 mmol) added in portions, followed by warming to room temperature and vigorous stirring for 6 hours. At this time, an aliquot was removed, decocted, and quantitatively analyzed by GC/MS. The resulting spectrum evinced a signal for the title compound at 25.1 min that corresponded to ~19% mass yield. Residual isoidide, octdecyl bromide and the elimination product, octadec-1-ene, also exhibited signals. Thin-layer chromatography (1:1 hexane/ethyl acetate) employing cerium molybdate stain manifested three salient spots, one near the solvent front consistent with octadecylbromide (and octadec-1-ene), one with rf=0.44 consistent with the title compound and one near the baseline, representing residual isoidide.

C. Isosorbide

Example 9: Synthesis of (3S,3aR,6R,6aR)-6-(octyloxy)hexahydrofuro[3,2-b]furan-3-ol+Isomer

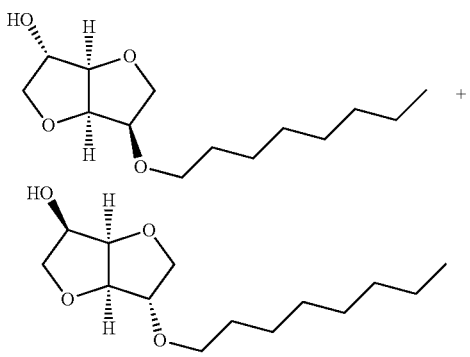

Experimental: A 20 cc scintillation vial equipped with a ½" egg-shaped PTFE coated magnetic stir bar was charged with 138 mg of isosorbide (0.94 mmol), 138 mg of potassium t-butoxide (1.23 mmol), 5 mL of dry DMF and stirred for 30 minutes. A rubber septum was then fitted to the vial mouth, the vial immersed in an ice/brine bath for 5 minutes, and 215 µL of octyl bromide (1.23 mmol) added dropwise, followed by warming to room temperature and vigorous stirring for 6 hours. At this time, an aliquot was removed, decocted, and quantitatively analyzed by GC/MS. The resulting spectrum evinced signals for the title compounds at 17.4 and 17.9 min that corresponded to mass yields of 14% and 17% respectively. Residual isosorbide, octyl bromide and some elimination product, oct-1-ene was also observed. Thin-layer chromatography (1:1 hexanes/ethyl acetate) employing cerium molybdate stain manifested four salient spots, one near the solvent front consistent with octylbromide and oct-1-ene), two with rfs=0.32, 0.34, consistent with the title compounds and one near the baseline, divulging remnant isosorbide.

Example 10: Synthesis of (3S,3aR,6R,6aR)-6-(decyloxy)hexahydrofuro[3,2]furan-3-ol+Isomer

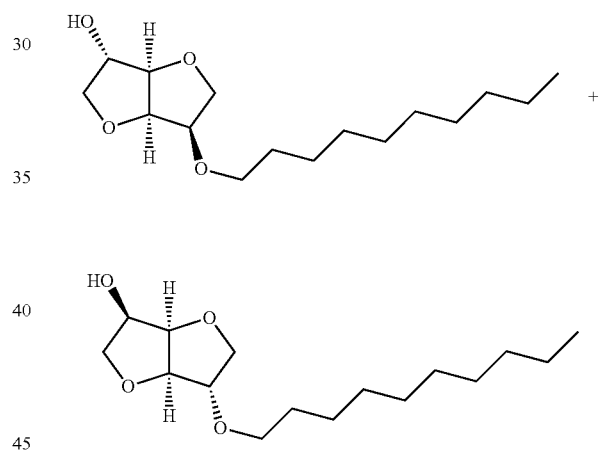

Experimental: A 20 cc scintillation vial equipped with a ½" egg-shaped PTFE coated magnetic stir bar was charged with 127 mg of isosorbide (0.87 mmol), 127 mg of potassium t-butoxide (1.13 mmol), 5 of dry DMF and stirred for 30 minutes. A rubber septum was then fitted to the vial mouth, the vial immersed in an ire/brine bath for 5 minutes, and 235 of decyl bromide (1.23 mmol) added dropwise, followed by warming to room temperature and vigorous stirring for 6 hours. At this time, an aliquot was removed, decocted, and quantitatively analyzed by GC/MS. The resulting spectrum evinced signals for the title compounds at 19.0 and 19.4 min that corresponded to mass yield of 14% and 19% respectively. Residual isosorbide, decyl bromide and some elimination product, dec-1-ene was also observed. Thin-layer chromatography (1:1 hexanes/ethyl acetate) employing cerium molybdate stain manifested four salient spots, one near the solvent front consistent with decylbromide (and dec-1-ene), two with rf=0.38 and 0.40 consistent with the title compounds and one near the baseline, indicating unreacted isosorbide.

Example 11: Synthesis of (3S,3aR,6R,6aR)-6-(dodecyloxy)hexahydrofuro[3,2-b]furan-3-ol+Isomer

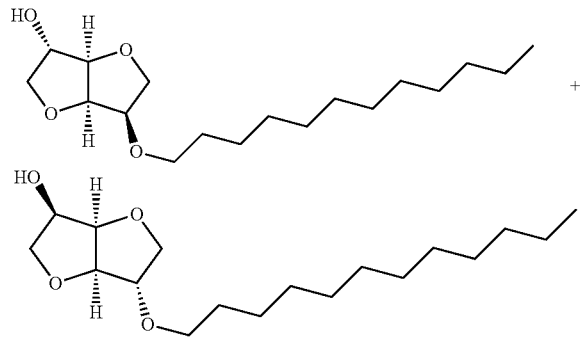

Experimental: A 20 cc scintillation vial equipped with a ½" egg-shaped PTFE coated magnetic stir bar was charged with 118 mg of isosorbide (0.81 mmol), 118 mg of potassium t-butoxide (1.05 mmol), 5 mL of dry DMF and stirred for 30 minutes. A rubber septum was then fitted to the vial mouth, the vial immersed in an ice/brine bath for 5 minutes, and 254 μL of dodecyl bromide (1.09 mmol) added dropwise, followed by warming to room temperature and vigorous stirring for 6 hours. At this time, an aliquot was removed, decocted, and quantitatively analyzed by GC/MS. The resulting spectrum manifested signals for the title compounds at 20.4 and 20.8 min that corresponded to mass yields of 15 and 18% respectively. Residual isosorbide, dodecyl bromide and some elimination product, dodec-1-ene was also observed. Thin-layer chromatography (1:1 hexanes/ethyl acetate) employing cerium molybdate stain manifested three salient spots, one near the solvent front consistent with dodecylbromide (and dodec-1-ene), two with rfs=0.40, 0.42 consistent with the title compounds and one near the baseline, specifying residual isosorbide.

Example 12: Synthesis of (3S,3aR,6R,6aR)-6-(octadecyloxy)hexahydrofuro[3,2-b]furan-3-ol+Isomer

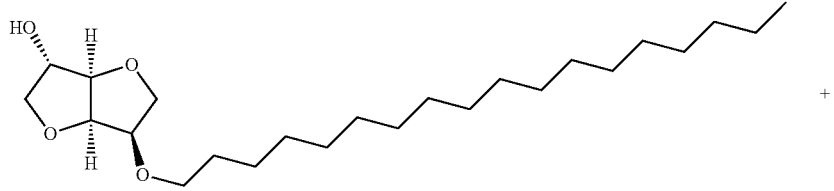

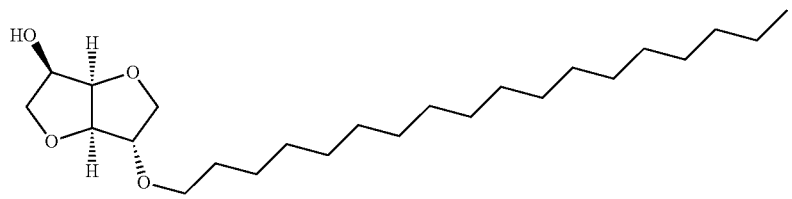

Experimental: A 20 cc scintillation vial equipped with a ½" egg-shaped PTFE coated magnetic stir bar was charged with 123 mg of isosorbide (0.84 mmol), 123 mg of potassium i-butoxide (1.09 mmol), 5 mL of dry DMF and stirred for 30 minutes. The vial was capped and immersed in an ice/brine bath for 5 minutes, and 365 mg of octadecyl bromide (1.09 mmol) added in portions, followed by warming to room temperature and vigorous stirring for 6 hours. At this time, an aliquot was removed, decocted, and quantitatively analyzed by GC/MS. The resulting spectrum revealed signals for the title compounds at 24.7 and 25.2 min that corresponded to mass yields of 11% and 13% respectively. Residual isosorbide, octadecyl bromide and some elimination product, octadec-1-ene was also observed. Thin-layer chromatography (1:1 hexanes/ethyl acetate) employing cerium molybdate stain manifested three salient spots, one near the solvent front consistent with octadecylbromide and octadec-1-ene), one with rf=0.44 consistent with the title compounds and one near the baseline, representing remnant isosorbide.

Comparative Example 1

Under the same reaction conditions, an experiment using sodium hydride, a highly reactive Brønsted base (pKa~36), in lieu of potassium t-butoxide was performed and evinced isomannide dioctyl diether with an exiguous amount of monooctyl ether.

Synthesis of (3R,3aR,6R,6aR)-6-(octyloxy)hexahydrofuro[3,2-b]furan-3-ol

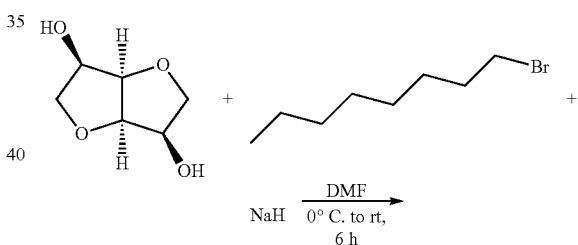

-continued

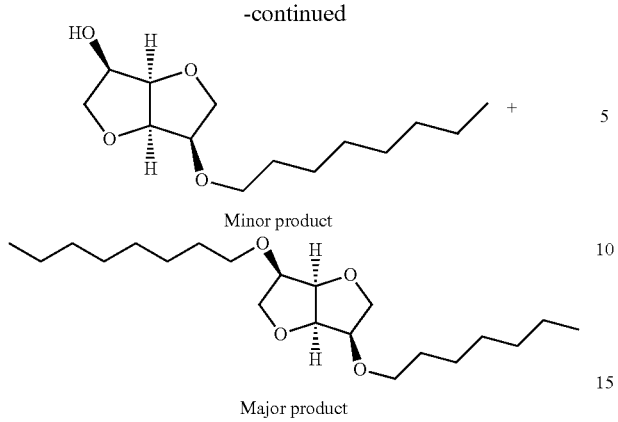

Minor product

Major product

Experimental: A 20 cc scintillation vial equipped with a ½" egg-shaped PTFE coated magnetic stir bar was charged with 110 mg of isomannide ((1.97 mmol), 43 mg of sodium hydride (60% in mineral oil, 1.06 mmol), 5 of dry DMF and stirred for 30 minutes. A rubber septum was then fitted to the vial mouth, the vial immersed in an ice/brine bath for 5 minutes, and 222 μL of octylbromide (1.26 mmol) added dropwise, followed by warming to room temperature and vigorous stirring for 6 hours. At this time, an aliquot was removed, decocted, and quantitatively analyzed by GC/MS. The resulting spectrum evinced a signal for the title compound at 16.3 min that corresponded to ~6% mass yield. The primary product was disclosed as the octyl diether of isomannide with ~27% mass yield and retention of 23.1 min. Significant amounts of residual isomannide and octylbromide were also observed.

The present invention has been described in general and in detail by way of examples. Persons of skill in the art understand that the invention is not limited necessarily to the embodiments specifically disclosed, but that modifications and variations may be made without departing tram the scope of the invention as defined by the following claims or their equivalents, including other equivalent components presently know or to be developed, which may be used within the scope of the invention. Therefore, unless changes otherwise depart from the scope of the invention, the changes should be construed as being included herein.

I claim:
1. An isohexide mono-ether comprising:

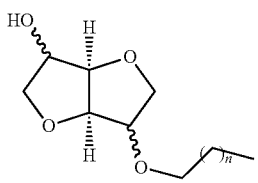

wherein when said isohexide is either isomannide or isoiodide "n" is an integer from 0 to 23, and when said isohexide is isosorbide "n" is an integer from 6 to 9, and 11 to 23.

2. The isohexide mono-ether according to claim 1, wherein said mono-ether is at least one of the following compounds:

a) where the isohexide contains isomannide:

1) (3R,3aR,6R,6aR)-6-(octyloxy)hexahydrofuro[3,2-b]furan-3-ol

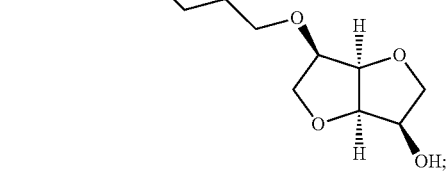

2) (3R,3aR,6R,6aR)-6-(decyloxy)hexahydrofuro[3,2-b]furan-3-ol

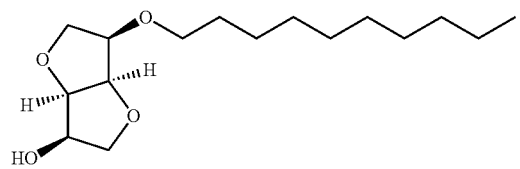

3) (3R,3aR,6R,6aR)-6-(dodecyloxy)hexahydrofuro[3,2-b]furan-3-ol

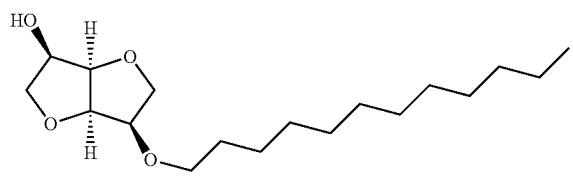

and 4) (3R,3aR,6R,6aR)-6-(octadecyloxy)hexahydrofuro[3,2-b]furan-3-ol

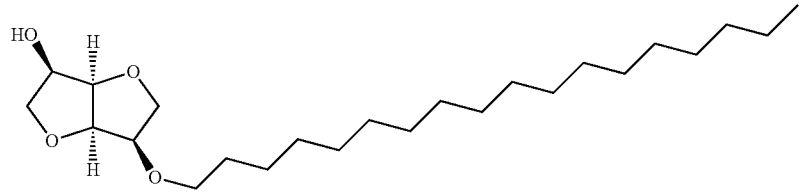

b) where the isohexide contains isoiodide:
1) (3S,3aR,6S,6aR)-6-(octyloxy)hexahydrofuro[3,2-b]furan-3-ol

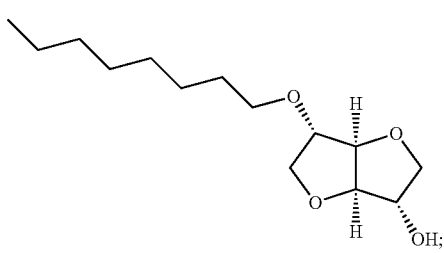 [SMILES: CCCCCCCCO[C@H]1CO[C@H]2[C@@H]1OC[C@@H]2O]

2) (3S,3aR,6S,6aR)-6-(decyloxy)hexahydrofuro[3,2-b]furan-3-ol

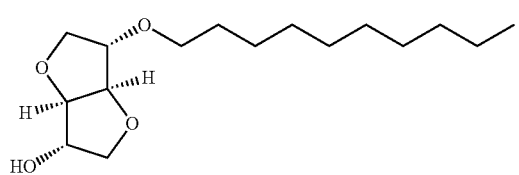

3) (3S,3aR,6S,6aR)-6-(dodecyloxy)hexahydrofuro[3,2-b]furan-3-ol

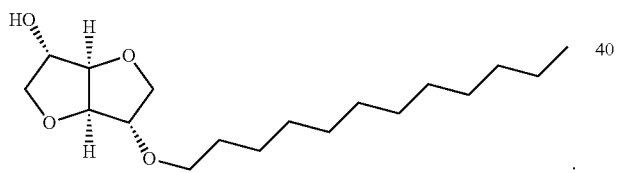

and
4) (3S,3aR,6S,6aR)-6-(octadecyloxy)hexahydrofuro[3,2-b]furan-3-ol

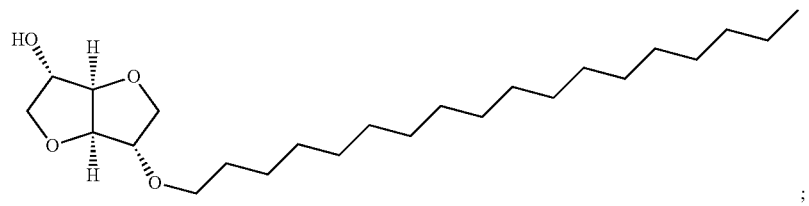 [SMILES: CCCCCCCCCCCCCCCCCCO[C@H]1CO[C@H]2[C@@H]1OC[C@@H]2O]

c) where the isohexide contains isosorbide:
1) (3S,3aR,6R,6aR)-6-(octyloxy)hexahydrofuro[3,2-b]furan-3-ol and Isomer

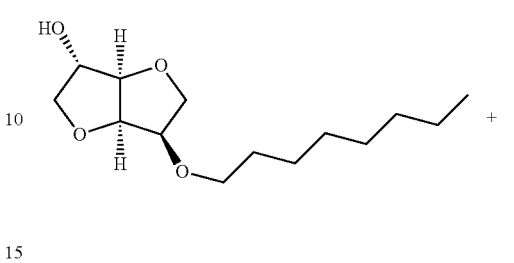

2) (3S,3aR,6R,6aR)-6-(decyloxy)hexahydrofuro[3,2-b]furan-3-ol and Isomer

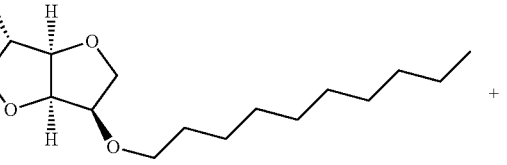

and
3) (3S,3aR,6R,6aR)-6-(octadecyloxy)hexahydrofuro[3,2-b]furan-3-ol and Isomer

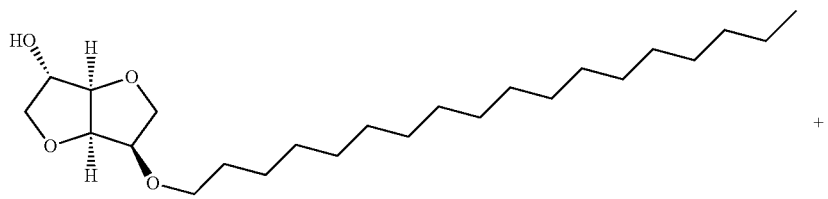
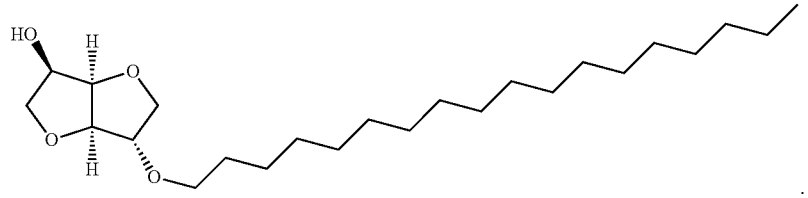
* * * * *